US00PP10824P

United States Patent [19]

Zerr

[11] Patent Number: Plant 10,824

[45] Date of Patent: Mar. 16, 1999

[54] POINSETTIA PLANT NAMED 'FISCOR CREME'

[75] Inventor: Katharina Zerr, Simmern, Germany

[73] Assignee: Florfis AG, Benningen, Switzerland

[21] Appl. No.: 854,673

[22] Filed: May 21, 1997

[51] Int. Cl.[6] ..... A01H 5/00

[52] U.S. Cl. ..... Plt./86.2

[58] Field of Search ..... Plt./86.2, 86.1

[56] References Cited

U.S. PATENT DOCUMENTS

| | | | |
|---|---|---|---|
| P.P. 8,319 | 7/1993 | Dahlquist | Plt./86.2 |
| P.P. 8,772 | 6/1994 | Jacobsen | Plt./86.2 |
| P.P. 9,364 | 11/1995 | Zerr | Plt./86.4 |

OTHER PUBLICATIONS

GTITM UPOVROM Citation for 'Fiscor Creme' as per CA PBR 96–909, Jul. 12, 1996.

GTITM UPOVROM Citation for 'Fiscor Creme' as per JP PBR 9138, Sep. 17, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of poinsettia plant named 'Fiscor Creme', characterized by its cream-white, weakly lobed bracts which are ovate to elliptically shaped to form a tight star-shaped involucre; uniform, weakly lobed dark green foliage; compact and low but wide growth habit, medium early flower response, and very good keeping quality.

1 Drawing Sheet

The present invention relates to a new and distinct cultivar of poinsettia plant, known by the cultivar name 'Fiscor Creme', and botanically known as *Euphorbia pulcherrima*.

'Fiscor Creme' is a product of a mutation induction program carried out by the inventor, Katharina Zerr, in Hillscheid, Germany, in 1994. The primary objective of the induction program was to expand the bract color ranges of 'Fiscor', a cultivar disclosed in U.S. Plant Pat. No. 9,364 and characterized by its dark red bract color, dark green foliage and comparatiavely compact habit.

The irradiation program comprised exposing rooted cuttings taken from plants of the parent cultivar to an X-ray source of 30 Gy dosage in Ahrensburg, Germany, under the supervision of the inventor. The irradiated plants were grown out in a greenhouse in Hillscheid, Germany, and were asexually propagated by taking cuttings. The plants resulting from these cuttings were screened for mutations as small flowering single stem plants in autumn and winter 1994 by the inventor, and identified by numbers. Parts of plants showing a positive mutation were left to develop vegetative shoots which are used as cuttings and grown out.

'Fiscor Creme' originated from a single white flowering plant (designated No. 647) which was discovered by the inventor in February 1995 among the vegetative off-spring of an earlier selected pink flowering plant from the above described mutation breeding program. By subsequent multiplication and checking for deviations, a uniform, white flowering clone was formed, which was examined and compared to other clones in a trial cultivation in summer 1995, and, on a larger scale, in autumn 1995.

It was confirmed that the combination of characteristics disclosed for 'Fiscor Creme' are firmly fixed and are retained through successive generations of asexual reproduction.

The following traits have been repeatedly observed and are determined to be basic characteristics of 'Fiscor Creme' which in combination distinguish this poinsettia as a new and distinct cultivar:

1. Cream white, weakly lobed bracts
2. Ovate to broad elliptically shaped bracts forming a tight star-shaped involucre
3. Uniform dark green foliage, weakly lobed.
4. Compact, and a comparatively low but wide growth habit 5. Medium early flowering response.
6. Very good keeping quality and retention of leaves and bracts 'Fiscor Creme' has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

Of the many commercial cultivars known to the inventor, the most similar in comparison to 'Fiscor Creme' are the parent variety 'Fiscor' (U.S. Plant Pat. No. 9,364) and the commercial varieties 'Lilo White' (U.S. Plant Pat. No. 8,319) and 'Freedom White' (U.S. Plant Pat. No. 8,772).

In contrast to the dark red colored bracts of 'Fiscor', 'Fiscor Creme' has cream-white bracts and light green petioles. The flowering response of 'Fiscor Creme' appears to be somewhat earlier and the plant habit slightly lower than 'Fiscor'. All other morphological characteristics are similar.

In comparison to 'Lilo White', branched plants of 'Fiscor Creme' are usually lower, but wider in shape, flower response is not quite as early as with 'Lilo White', the cyathia retention is better, and 'Fiscor Creme' has creamier cream-white bracts compared to the more yellow-white bracts of 'Lilo White'.

In comparison to 'Freedom White', 'Fiscor Creme' has smaller bracts with a more smooth surface, creamier cream-white bract color, and a later flower response. In addition, 'Fiscor Creme' develops more cyathia with better retention characteristics, and the plant habit of 'Fiscor Creme' is usually lower than that of 'White Freedom'

The accompanying color photographic drawing is a top perspective view showing typical inflorescence and foliage of 'Fiscor Creme', with colors being as true as possible with illustrations of this type. The photograph illustrates a typical mature potted plant.

The following description is based on plants planted as rooted cuttings in 12 cm pots on Aug. 24, 1995, pinched 14 days later leaving 8 nodes, and grown at 17°–20° C. minimum day and night temperatures. The plants initiated flowers under natural short day conditions in autumn. Observations and measurements were mainly taken at the beginning of flowering.

In the following description, color references are made to The Royal Horticultural Society Colour Chart. The color values were determined indoors in a north light, with the bract color values being based on plants grown at 17° C.

Classification:

*Botanical.*—*Euphorbia pulcherrima.*

*Commercial.*—Poinsettia, cv. 'Fiscor Creme'.

Parentage: Induced mutation of 'Fiscor'.

Plant description:

*Form.*—Shrub, self-branching.

*Growth habit.*—Compact, medium height; pinched plants are bushy and broad; weak to medium growth; Height (above the soil line): 22.0 cm. Width: 46.0 cm. Average no. of branches: 5.3.

*Stem color.*—Solid green with no anthocyanin.

*Rooting.*—Medium, 20–24 days.

*Blooming habit.*—The commencement of flowering under natural short day conditions in autumn: Botanically (cyathia open): around December 1. Commercially (bracts colored, marketable): late November. Flowering response time: about 9 weeks.

*Flowering season and keeping quality.*—Under winter conditions in Central Europe, commercial quality will be maintained for about 4–6 weeks from date when plant is ready for sale in late November; however, under controlled conditions with sufficient light intensity, the flowering period may be expanded by several weeks; leaf and bract retention is generally better under poor light conditions than that of most similar cultivars with medium green foliage.

*Foliage.*—Shape: Broad elliptical, with weak lobes and rounded base. Size: Leaf blade: Length: 13.0 cm. Width: 7.5 cm. Petiole: 6.5 cm. Color: Dark green. Upper surface: about 147 A. Under surface: about 147 B. Leaf petiole: Light green, about 147 D. Texture: surface smooth and flat. Edge of margin: Entire. Leaf surface and venation: Upper surface: Smooth and flat, only weakly veined with light green, about R.H.S. 146 D. Under surface: Flat and smooth, except for the slightly protruding midrib and finer side veins, which protrude at an acute, almost right angle from the midrib; the side veins are evenly spread throughout the leaf blade and run parallel to each other; vein color is R.H.S. 146 C.

Flowering description:

*Cyathia.*—In a narrow cluster, few (about 10–14); retention is average when compared to similar cultivars of this variety.

*Bracts.*—Larger bracts are ovate or broad elliptical in shape, with weak lobes and rounded base; flat.

*Size.*—Largest bract with petiole: 15.8 cm; bract length is about 14.3 cm; petiole length is about 1.5 cm; and bract width is about 9.2 cm.

*Color.*—Cream-white. Upper surface: about 10 D. Lower surface: about 4 D.

*Aspect.*—Horizontal, forming a star-shaped involucre with a tight (well-closed) center where the bracts meet the stem.

*Bract venation and color.*—The bracts are smooth and flat with veins hardly visible during dehiscence. As bract leaves mature, veins create a more rugose pattern similar to the foliage leaves. Vein color corresponds closely to bract color, upper surface veins are 10 D and lower surface veins are 4 D. Mature, fully colored bracts tend to keep their color, fading very little. Bracts that are still growing may become green within about 3 weeks when the plants are exposed to long-day conditions, depending primarily on light intensity.

Reproductive organs:

*Nectar cups.*—Medium sized, yellow.

*Stamens.*—Filaments whitish.

*Pollen.*—Yellow.

*Pistils.*—Style and stigma whitish, 6-lobed stigma.

*Ovaries.*—Light to medium green in color; triangular, 3-celled, 3 ovules.

I claim:

1. A new and distinct cultivar of poinsettia plant named 'Fiscor Creme', as illustrated and described.

* * * * *

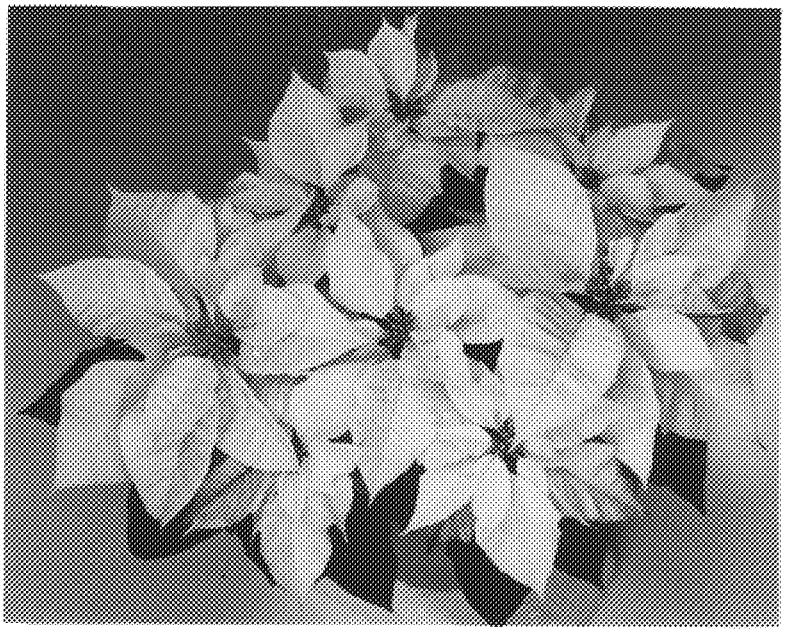

UNITED STATES PATENT AND TRADEMARK OFFICE

CERTIFICATE OF CORRECTION

PATENT NO. : PP 10,824

DATED : March 16, 1999

INVENTOR(S) : Katharina ZERR

It is certified that error appears in the above-indentified patent and that said Letters Patent is hereby corrected as shown below:

On the title page, Item [22], Filed, contains a typographical error wherein "May 21, 1997" should read --May 12, 1997--.

Signed and Sealed this

Fifteenth Day of February, 2000

*Attest:*

Q. TODD DICKINSON

*Attesting Officer*

*Commissioner of Patents and Trademarks*